(12) United States Patent
Abraham et al.

(10) Patent No.: US 11,331,334 B2
(45) Date of Patent: May 17, 2022

(54) INTRANASAL COMPOSITION OF METHYLCOBALAMIN

(71) Applicant: TORRENT PHARMACEUTICALS LTD., Ahmedabad (IN)

(72) Inventors: Jaya Abraham, Dist. Gandhinagar (IN); Vivek Mishra, Dist. Gandhinagar (IN); Kiran Chaudhari, Dist. Gandhinagar (IN); Vipul Mittal, Dist. Gandhinagar (IN)

(73) Assignee: TORRENT PHARMACEUTICALS LTD.

( * ) Notice: Subject to any disclaimer, the term of this patent is extended or adjusted under 35 U.S.C. 154(b) by 30 days.

(21) Appl. No.: 16/482,491

(22) PCT Filed: Feb. 5, 2018

(86) PCT No.: PCT/IB2018/050701
§ 371 (c)(1),
(2) Date: Jul. 31, 2019

(87) PCT Pub. No.: WO2018/142358
PCT Pub. Date: Aug. 9, 2018

(65) Prior Publication Data
US 2020/0009179 A1    Jan. 9, 2020

(30) Foreign Application Priority Data

Feb. 6, 2017    (IN) .............................. 201721004210

(51) Int. Cl.
*A61K 31/714*    (2006.01)
*A61K 9/00*    (2006.01)
*A61K 47/10*    (2017.01)
*A61K 47/36*    (2006.01)
*A61K 47/44*    (2017.01)

(52) U.S. Cl.
CPC .......... *A61K 31/714* (2013.01); *A61K 9/0043* (2013.01); *A61K 47/10* (2013.01); *A61K 47/36* (2013.01); *A61K 47/44* (2013.01)

(58) Field of Classification Search
CPC ....... A61K 31/714; A61K 47/10; A61K 47/36
See application file for complete search history.

(56) References Cited

U.S. PATENT DOCUMENTS 7,229,636 B1    6/2007  Quay et al.
2013/0131007 A1*  5/2013  Brown .................. A61K 9/006
                                                     514/48

FOREIGN PATENT DOCUMENTS

WO    WO 2012/056299 A1    5/2012

OTHER PUBLICATIONS

Kuzminski, et al., Blood, vol. 92, No. 4 Aug. 15, 1998: pp. 1191-1198.
International Search Report dated May 11, 2018, for corresponding International Patent Application No. PCT/IB2018/050701.
Written Opinion dated May 11, 2018 for corresponding International Patent Application No. PCT/IB/2018/050701.

* cited by examiner

*Primary Examiner* — Pancham Bakshi
(74) *Attorney, Agent, or Firm* — Pergament & Cepeda LLP; Milagros A. Cepeda; Edward D. Pergament

(57) ABSTRACT

The present invention relates to an intranasal composition, particularly once weekly intranasal composition comprising methylcobalamin and at least one gelling agent and a process for preparation thereof.

12 Claims, 1 Drawing Sheet

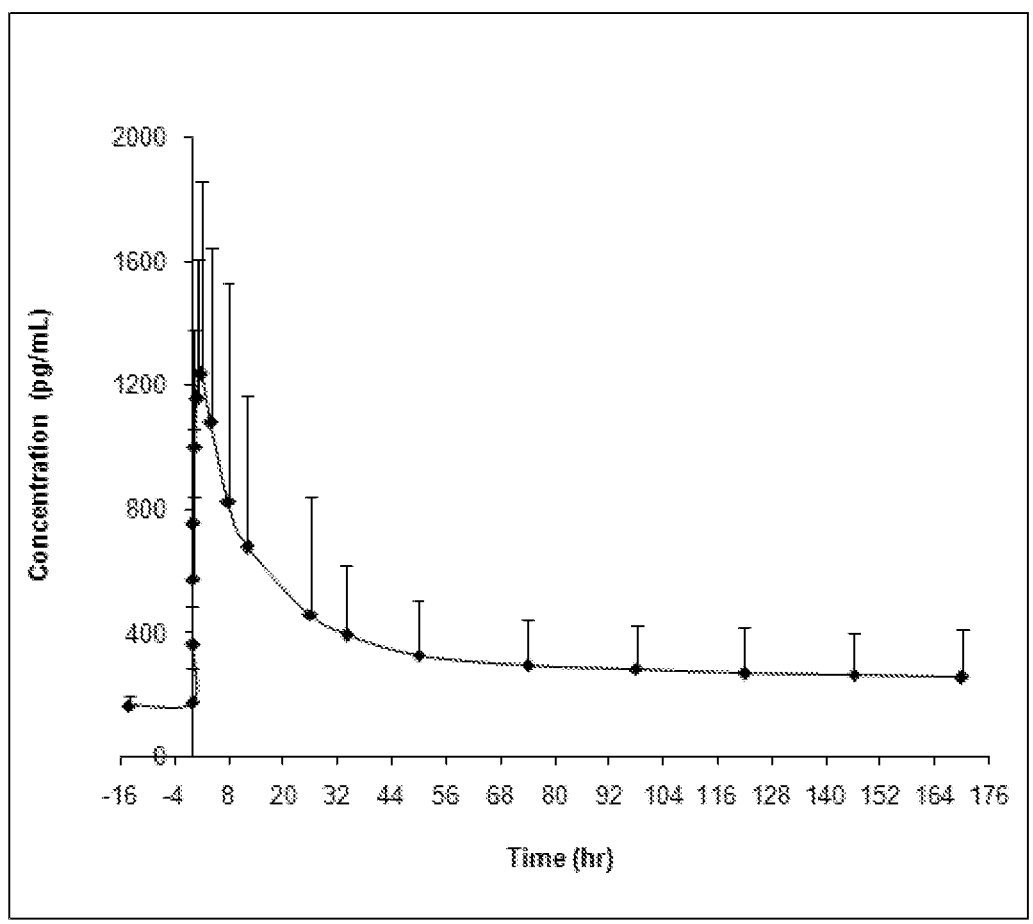

INTRANASAL COMPOSITION OF METHYLCOBALAMIN

This application is a National Stage Application under 35 U.S.C. § 371 of PCT International Application No. PCT/IB2018/050701, filed Feb. 5, 2018, which takes priority from Indian Provisional Application Number IN 201721004210, filed Feb. 6, 2017, all of which is herein incorporated in its entirety.

FIELD OF THE INVENTION

The present invention relates to an intranasal composition comprising methylcobalamin. More particularly the present invention relates to once weekly intranasal composition comprising methylcobalamin and at least one gelling agent and a process for preparation thereof.

BACKGROUND

Vitamin B12 or cobalamin is essential for cellular DNA synthesis and hence contributes to functions of various tissues of the body, formation of myelin sheath, more so the rapidly dividing and proliferating cellular systems such as blood and gastric epithelium and its deficiency leads to anemia or peripheral neuropathy. Daily requirement of vitamin B12 is about 1-3 micrograms. Clinically, persons having 200 picogram (pg) or more cobalamin plasma concentration can be referred as normal and those having less than 200 pg concentration of vitamin B12 are categorized as deficient persons. (Kuzminski et al; Blood, Vol 92, No 4 (Aug. 15), 1998: pp 1191-1198).

Cobalamin occurs in two main forms, hydroxocobalamin and cyanocobalamin. Cyanocobalamin is converted in the body to methylcobalamin or adensoylcobalamin by the removal of the cyanide molecule. Methylcobalamin is the most active and primary form, accounting for as much as 60-80%.

Human body does not synthesize cobalamin. The only source is food of animal origin, such as meat, fish and dairy products. Dietary cobalamin deficiency arises in vegetarians who do not touch meat, fish, egg and cheese. The largest group in the world consists of Indian vegetarians. Broadly the two main causes of cobalamin deficiency in India include nutrition lacking in vitamin B12 due to large section of Indian society adopting vegetarianism, secondly malabsorption due to various diseases.

Therefore, to overcome deficiency of vitamin B12, it is required to provide an external supplement of cobalamin such as in the form of cyanocobalamin and methylcobalamin, which can achieve and maintain levels of cobalamin above 200 pg. Methylcobalamin has advantage over cyanocobalamin as significantly more cobalamin accumulates in liver tissue following administration of methylcobalamin, as compared to cyanocobalamin.

There are many dosage forms available for cyanocobalamin and methylcobalamin supplements such as oral or injectable composition. Oral dosage forms include tablets, capsule, syrups, liquids, drops etc, however, since intrinsic factor is absent in patients who have pernicious anemia; oral preparations will be ineffective because absorption of vitamin B12 in gastrointestinal tract (GIT) occurs by binding with intrinsic factor (an active process). For other forms such as injections and infusions, problem of patient compliance arises as it requires physician's intervention.

Some alternate dosage form such as intranasal compositions of cyanocobalamin and methylcobalamin have also been disclosed in U.S. Pat. No. 7,229,636 and WO2012056299.

All of the above mentioned dosage forms are administered daily or on alternate day to patients during initial period of treatment, for achieving blood levels of more than 200 pg cobalamin, and later administration can be extended for once a week regimen for maintenance of such levels. For example, Nascobal, a nasal spray, available in the USA market is recommended for once a week dosing, however, before initiating nasal dose, patients were given injections of cyanocobalamin to achieve therapeutic levels of cobalamin.

Such types of therapies are not patient compliant as switching in dosage form is not patient friendly and self-administration is not possible in case of injections. Further, such split dosing creates confusion in patients and they may miss one or two doses, or may start once week dosing regimen earlier or later than recommendation.

Therefore, there is a need of a dosage form which is more patient complaint, suitable for self-administration and provides therapeutic levels of cobalamin after single administration.

SUMMARY OF THE INVENTION

One aspect of the present invention is to provide an intranasal composition comprising methylcobalamin, at least one gelling agent and optionally a permeation enhancer selected from lecithin and di-ethylene glycol monoethyl ether, wherein the composition forms in-situ gel after intranasal administration.

Preferably, the intranasal composition is administered once weekly.

Another aspect of the present invention is to provide an intranasal composition comprising methylcobalamin, at least one gelling agent and a permeation enhancer selected from lecithin and di-ethylene glycol monoethyl ether, wherein the composition forms in-situ gel after intranasal administration.

Another aspect of the present invention is to provide once weekly intranasal composition comprising methylcobalamin, at least one gelling agent and a permeation enhancer selected from lecithin and di-ethylene glycol monoethyl ether, wherein the composition provides and maintains mean plasma concentration of cobalamin about 200 pg/mL or more for at least 7 days.

Another aspect of the present invention provides once weekly intranasal composition comprising methylcobalamin, at least one gelling agent and a permeation enhancer selected from lecithin and di-ethylene glycol monoethyl ether, for the treatment of Vitamin B12 deficiency wherein, the treatment does not require daily or alternate day regime during initial period of treatment.

Another aspect of the present invention provides once weekly intranasal composition comprising methylcobalamin and gellan gum.

Another aspect of the present invention provides once weekly intranasal composition comprising methylcobalamin and a permeation enhancer selected from lecithin and di-ethylene glycol monoethyl ether.

Another aspect of the present invention provides a process for preparation of intranasal composition comprising methylcobalamin and at least one gelling agent.

Another aspect of the present invention provides a method of treating vitamin B12 deficiency by intranasally administering a composition comprising methylcobalamin, at least one gelling agent and optionally a permeation enhancer selected from lecithin and di-ethylene glycol monoethyl ether, wherein the composition forms in-situ gel after intranasal administration.

These and other aspects of the invention may be more clearly understood from the following detailed description, from the examples given for illustrative and non-limiting purposes and the appended drawing and claims.

BRIEF DESCRIPTION OF THE DRAWINGS

The present invention may be better understood by reference to the drawing in combination with the detailed description of the specific embodiment presented herein.

FIG. 1: Is a graph depicting mean plasma concentration of Cobalamin on intranasal administration of composition of Example 1 to human subjects.

DETAILED DESCRIPTION OF THE INVENTION

The following paragraphs detail various embodiments of the invention. For the avoidance of doubt, it is specifically intended that any particular feature(s) described individually in any one of these paragraphs (or part thereof) may be combined with one or more other features described in one or more of the remaining paragraphs (or part thereof). In other words, it is explicitly intended that the features described below individually in each paragraph (or part thereof) represent important aspects of the invention that may be taken in isolation and combined with other important aspects of the invention described elsewhere within this specification as a whole, and including the examples and figures. The skilled person will appreciate that the invention extends to such combinations of features and that these have not been recited in detail here in the interests of brevity.

The use of the terms "a" and "an" and "the" and similar referents in the context of describing the invention (especially in the context of the following claims) are to be construed to cover both the singular and the plural, unless otherwise indicated herein or clearly contradicted by context.

Throughout this specification and the appended claims, it is to be understood that the words "comprise", "have" and "include" and variations such as "comprises", "comprising", "having" "includes", "including" are to be interpreted inclusively, unless the context requires otherwise. That is, the use of these words may imply the inclusion of an element or elements not specifically recited.

The term "cobalamin" as used herein includes total vitamin B12 which may include one or more than one isoforms of cobalamin including hydroxocobalamin, cyanocobalamin, methylcobalamin or adenosylcobalamin.

The term "mean plasma concentration" as used herein refers to an arithmetic average of a set of values obtained as individual plasma concentration at a specific time, derived from an adequate number of subjects.

The term "in-situ gel" as used herein refers to gel, semisolid or solid structure formed when a pharmaceutical composition once administered to a human being undergo gelation in situ and intended to remain at the site of administration and release the drug for a longer period of time in the mammalian body.

The term "w/v" as used herein means weight of component by total volume of a composition, unless specified otherwise.

The present invention provides an intranasal composition comprising methylcobalamin, at least one gelling agent and optionally a permeation enhancer selected from lecithin and di-ethylene glycol monoethyl ether, wherein the composition forms in-situ gel after intranasal administration.

In one embodiment the present invention provides an intranasal composition comprising methylcobalamin, at least one gelling agent and a permeation enhancer selected from lecithin and di-ethylene glycol monoethyl ether, wherein composition forms in-situ gel after intranasal administration.

Preferably, gellan gum is used as a gelling agent.

Preferably, the intranasal composition is administered once weekly.

In another embodiment the present invention provides an intranasal composition comprising about 0.01 to 0.5% w/v of methylcobalamin.

Preferably, the composition comprises about 0.01 to about 0.45% w/v of methylcobalamin. More preferably, the composition comprises about 0.05 to 0.25% w/v of methylcobalamin. Most preferably, the composition comprises about 0.25% w/v of methylcobalamin.

In another embodiment the present invention provides a method of treating vitamin B12 deficiency by intranasally administering the composition comprising methylcobalamin, at least one gelling agent and optionally a permeation enhancer selected from lecithin and di-ethylene glycol monoethyl ether, wherein the composition forms in-situ gel after intranasal administration.

In another embodiment the present invention provides a use of an intranasal composition comprising methylcobalamin, at least one gelling agent and optionally a permeation enhancer selected from lecithin and di-ethylene glycol monoethyl ether, for the treatment of Vitamin B12 deficiency, wherein the composition forms in-situ gel after intranasal administration.

In another embodiment the present invention provides a composition of methylcobalamin for once weekly intranasal administration in humans, which comprises at least one gelling agent and a permeation enhancer selected from lecithin and di-ethylene glycol monoethyl ether. The composition of present invention provides therapeutic level of cobalamin in single administration of the composition to one nostril or each nostril and maintains it for at least 7 days.

In another embodiment the present invention provides a once weekly intranasal composition comprising methylcobalamin, at least one gelling agent and a permeation enhancer selected from lecithin and di-ethylene glycol monoethyl ether, wherein the composition provides and maintains mean plasma concentration of cobalamin about 200 pg or more for at least 7 days.

The composition comprising methylcobalamin according to the present invention provides a therapeutic mean plasma concentration of cobalamin equal to or above required levels that is about 200 pg for at least 7 days, thereby reduces frequency of administration of dose and improves patient compliance. Such composition also eliminates need for alternate dosage form during initial time period of treatment.

Thus, in another embodiment the present invention provides a once weekly intranasal composition comprising methylcobalamin, at least one gelling agent and a permeation enhancer selected from lecithin and di-ethylene glycol monoethyl ether, for the treatment of vitamin B12 deficiency wherein, the treatment does not require daily or alternate day regime during initial period of treatment.

The gelling agent used according to the present invention is such that it makes gel in-situ after administration of the composition intranasally. Such in-situ gel may increase the residence time of the composition on the nasal mucosa. For achieving 7 days profile, slow rate of absorption of methylcobalamin is required to increase the absorption time. It was surprisingly found that the composition according to present invention increases $C_{last}$ (last observed plasma concentration) and $T_{last}$ (time of the last observed plasma concentration) therefore maintains therapeutic concentration of cobalamin equal to or above required levels for 7 days.

Suitable gelling agent according to the present invention includes gellan gum, xyloglucan, alginic acid, sucrose crosslinked pectin, poloxamers or the like or the mixture thereof. Preferably, the gelling agent is gellan gum. Gelling agent can be used in quantity sufficient to form gel like structure on the nasal mucosa. Preferably the gelling agent is present in the composition in an amount of about 0.1% to 1% w/v of total composition.

In another embodiment the present invention provides a once weekly intranasal composition comprising methylcobalamin and gellan gum.

In certain embodiments of the present invention the intranasal composition comprises a permeation enhancer selected from lecithin and di-ethylene glycol monoethyl ether. Without binding to any theory, these permeation enhancers help in increasing nasal permeability which helps in absorption of drug in such a way that desirable concentration of cobalamin is retained up to 7 days.

Therefore, in another embodiment the present invention provides a once weekly intranasal composition comprising methylcobalamin and a permeation enhancer selected from lecithin and di-ethylene glycol monoethyl ether.

Some additional/alternative permeation enhancers may also be used in the composition selected from but not limiting to chitosan, poloxamer, heptyl glucoside (Sepiclear), polyoxyethylene sorbitan monolaurate (Tween 20, Tween 60, Tween 80), dimethyl isosorbide, caprylocaproyl polyoxyl-8 glycerides (Labrasol®), cyclodextrin, cyclic urea and amino acids. Amino acids such as glycine, cysteine, leucine, isoleucine, alpha-amino butyric acid, or the like can be used as permeation enhancer.

Permeation enhancers can be used in an amount ranging from about 0.01%-10% w/v of total composition, preferably from about 0.1-10% w/v. In an embodiment the permeation enhancer is included in an amount ranging from about 0.1-1% w/v of the composition. Most preferably, lecithin (Lipoid S-100) is used as permeation enhancer in the quantity of about 0.50% w/v of the total composition. Lecithin includes group of fatty substances occurring in animal and plant tissues which are amphiphilic. Generally, Lecithin is a mixture of phospholipids in oil and the composition depends on its origin. The main phospholipids in lecithin are phosphatidyl choline, phosphatidyl inositol, phosphatidyl ethanolamine, and phosphatidic acid. Besides these, lecithin may also consist of triglycerides and smaller amount of one or more other non-phospholipid compounds such as carbohydrates, pigments, free fatty acids, free sterols, sterol glycosides, tocopherol etc.

The once weekly composition according to present invention may further comprise pharmaceutically acceptable excipients selected from thickening agent, humectant, preservative, flavoring agent and vehicle.

In another embodiment the present invention provides a once weekly intranasal composition comprising methylcobalamin, gelling agent, permeation enhancer, thickening agent, humectant, preservative and vehicle.

In yet another embodiment the present invention provides a once weekly intranasal composition comprising of methylcobalamin, gelling agent, permeation enhancer, thickening agent, humectant, flavoring agent, preservative and vehicle.

In an embodiment the amount of thickening agent present is from about 0.1% to about 1% w/v of the composition. In a preferred embodiment, the thickening agent is included in an amount of about 0.20% w/v of the composition, In an embodiment the amount of humectant present is from about 1% to about 5% w/v of the composition. In a preferred embodiment, the humectant is included in an amount of about 2.0% w/v of the composition.

In an embodiment the amount of preservative present is from about 0.01 to about 1% w/v of the composition. In a preferred embodiment, the preservative is present in an amount of about 1.0% w/v of the composition.

In an embodiment the intranasal composition comprises about 0.01% to about to 0.5% w/v of methylcobalamin, about 0.1% to about 1% w/v of gelling agent, about 0.1% to about 1% w/v of thickening agent, about 1% to about 5% w/v of humectant, about 0.01% to about 1% w/v of preservative, about 0.1% to about 1% w/v of permeation enhancer.

In an embodiment the intranasal composition comprises about 0.05% to about 0.25% w/v methylcobalamin, about 0.40% w/v gelling agent, about 0.20% w/v thickening agent, about 2.0% w/v humectant, about 1.0% w/v preservative, about 0.50% w/v permeation enhancer, based on total volume of composition.

Thickening agent according to the present invention includes naturally-occurring polymeric materials such as, locust bean gum, sodium alginate, sodium caseinate, egg albumin, gelatin agar, carrageenin gum, quince seed extract, starch, chemically modified starches and the like; semi-synthetic polymeric materials such as cellulose ethers (e.g. hydroxyethyl cellulose, methyl cellulose, carboxymethyl cellulose, hydroxy propylmethyl cellulose), polyvinylpyrrolidone, polyvinylalcohol, guar gum, hydroxypropyl guar gum, soluble starch, cationic celluloses, cationic guars and the like and synthetic polymeric materials such as carboxyvinyl polymers, polyvinylpyrrolidone, polyvinyl alcohol polyacrylic acid polymers, polymethacrylic acid polymers, polyvinyl acetate polymers, polyvinyl chloride polymers, polyvinylidene chloride polymers and the like and hyaluronic acid. A thickening agent may be used in the range of about 0.1 to about 1% w/v. In an embodiment, the thickening agent is preferably hydroxypropyl methyl cellulose. In a preferred embodiment, the thickening agent is hydroxypropyl methyl cellulose included in an amount of 0.20% w/v.

Humectant according to the present invention includes cetyl palmitate, glycerol (glycerin), PPG-15 stearyl ether, lanolin alcohol, lanolin, lanolin derivatives, cholesterol, petrolatum, isostearyl neopentanoate, octyl stearate, mineral oil, isocetyl stearate, myristyl myristate, octyl dodecanol, 2-ethylhexyl palmitate (octyl palmitate), dimethicone, phenyl trimethicone, cyclomethicone, $C_{12}$-$C_{15}$ alkyl benzoates, dimethiconol, ethylene glycol, propylene glycol, hexylene glycol, theobroma grandiflorum seed butter, ceramides (e.g., ceramide 2 or ceramide 3), hydroxypropyl bispalmitamide MEA, hydroxypropyl bislauramide MEA, hydroxypropyl bisisostearamide MEA, 1,3-bis(N-2-(hydroxyethyl)stearoylamino)-2-hydroxy propane, bis-hydroxyethyl tocopherylsuccinoylamido hydroxypropane, urea, aloe, allantoin, glycyrrhetinic acid, and dicaprylate/dicaprate. A humectant is used in the range of about 1 to 5% w/v. In an embodiment, the humectant is preferably glycerin. In a preferred embodiment, the humectant is preferably glycerin included in amount of 2.00% w/v.

Preservative for use in the present invention is chosen in quantities that preserve the composition. Suitable preservatives according to present invention include, but are not limited to, benzalkonium chloride, methyl, ethyl, propyl or butylparaben, benzyl alcohol, phenylethyl alcohol, benzethonium, chlorobutanol, potassium sorbate or combination thereof. Preferably, preservative is selected from benzyl alcohol, phenyl ethyl alcohol or their mixture.

The flavoring agent according to invention may be chosen from natural and synthetic flavoring liquids such as volatile oils, synthetic flavor oils, flavoring aromatic and oils, liquids, oleoresins or extracts derived from plants, leaves, flowers, fruits, stems and combinations thereof. Non-limiting representative examples of volatile oils include spearmint oil (Novamint Spearmint), cinnamon oil, oil of wintergreen (methyl salicylate), peppermint oil, menthol, lavender, lotus, rose, saffron, jasmine, eugenol, clove oil, bay oil, anise oil, eucalyptus oil, thyme oil, cedar leaf oil, oil of nutmeg, allspice oil, oil of sage, mace extract, oil of bitter almond, and cassia oil. Various artificial, natural or synthetic flavors can also be used including fruit flavors such as vanilla, and citrus oils including lemon, orange, grape, lime and grapefruit and fruit essences including apple, pear, peach, grape, strawberry, raspberry, cherry, plum, pineapple, apricot and so forth. Other useful flavoring agents include aldehydes and esters such as benzaldehyde (cherry, almond), citral, i.e., alphocitral (lemon, lime), neral, i.e., beta-citral (lemon, lime), decanal (orange, lemon), aldehyde C-8 (citrus fruits), aldehyde C-9 (citrus fruits), aldehyde C-12 (citrus fruits), tolyl aldehyde (cherry, almond), 2,6-dimethyloctanal (green fruit), and 2-dodecenal (citrus, mandarin), or the like or the mixtures thereof.

Vehicle according to present invention include, but are not limited to, saline, water, dextrose or combinations thereof. A preferred vehicle is purified water or water for injection. The amount of vehicle depends on the amounts of the other ingredients present in the nasal composition. The amount of vehicle is a sufficient amount (q.s.) that is required to establish a specified volume.

In an another embodiment the present invention provides a once weekly intranasal composition comprising about 0.05% to about 0.25% w/v methylcobalamin, about 0.40% w/v gellan gum, about 0.20% w/v hydroxypropyl methyl cellulose, about 2.0% w/v glycerin, about 0.50% w/v benzyl alcohol, about 0.50% w/v lecithin and water, based on total volume of composition.

In another embodiment the present invention provides a once weekly intranasal composition comprising about 0.05% to about 0.25% w/v methylcobalamin, about 0.40% w/v gellan gum, about 0.20% w/v hydroxypropyl methyl cellulose, about 2.0% w/v glycerin, about 0.50% w/v benzyl alcohol, about 0.50% phenyl ethyl alcohol, about 0.50% w/v lecithin and water, based on total volume of composition.

In another embodiment the present invention provides a once weekly intranasal composition comprising about 0.05% to about 0.25% w/v methylcobalamin, about 0.40% w/v gellan gum, about 0.20% w/v hydroxypropyl methyl cellulose, about 2.0% w/v glycerin, about 0.50% w/v benzyl alcohol, about 0.50% phenyl ethyl alcohol, about 0.50% w/v lecithin and about 0.01% to about 0.2% flavoring agent and water based on total volume of composition.

Any suitable process known to a person skilled in the art of pharmaceutical science may be used for the preparation of compositions of the present invention. Preferably compositions can be prepared by mixing methylcobalamin and one or more excipients as described herein above.

Generally, the composition of is prepared by mixing gelling agent in a vehicle, optionally including and mixing preservative and humectant. Optionally, thickening agent may be added in the obtained solution or suspension. Further, methylcobalamin and a permeation enhancer is added in the obtained solution or suspension and making the volume to 100% using vehicle.

The pH of the composition of the present invention ranges from 4 to 5.5. Preferably, pH is less than 5.5, most preferably pH of the composition is 5.

The intranasal composition can be formulated in any suitable form such as aqueous composition for in-situ gel, or gel composition. Alternatively powder composition, liposomes, micoremulsions or nanoemulsion may be prepared.

The composition obtained can be filled in suitable container attached with nasal spray pump or any other suitable applicator. Container for example may be a multi dose container or a unit dose container capable of delivering a metered volume of the intranasal composition.

In an embodiment, the present invention provides a method of treating of vitamin B12 deficiency by intranasally administering a composition in accordance with the present invention comprising methylcobalamin, at least one gelling agent and optionally a permeation enhancer selected from lecithin and di-ethylene glycol monoethyl ether, wherein the composition forms in-situ gel after intranasal administration.

Amount of methylcobalamin to be delivered through single nostril or each nostril is 0.25 to 0.5 mg, preferably 0.5 mg, for achieving effective mean plasma concentration of cobalamin to treat vitamin B deficiency.

The composition of present invention comprises methylcobalamin ranging from 10 microgram/mL to 5000 microgram/mL. Preferably, the composition comprises from 10 microgram/mL to 4500 microgram/mL, more preferably the composition comprises 10 microgram/mL to 2500 microgram/mL of methylcobalamin, most preferably the composition comprises about 2500 microgram/mL of methylcobalamin.

Once weekly intranasal composition of the present invention is delivered in volume of 25 microliters to 200 microliters. Preferably, volume of delivery of intranasal composition of the present invention is 100 microliters. The volume of administration of the intranasal composition with the help of suitable container for example as described above helps in delivering the required dose, at required concentration without causing spilling of methylcobalamin.

The intranasal administration of the composition in accordance with the present invention provides and maintains mean plasma concentration of cobalamin of about of 200 pg or more for at least 7 days.

In an embodiment, the present invention provides use of intranasal composition comprising methylcobalamin, at least one gelling agent and optionally a permeation enhancer selected from lecithin and di-ethylene glycol monoethyl ether, for the treatment of Vitamin B12 deficiency wherein, the composition forms in-situ gel after intranasal administration. In certain embodiments, the invention provides use of intranasal composition of the present invention in the manufacture of medicament to be adapted for delivering the requisite dose of methylcobalamin intranasal at specific interval for providing the patient friendly regimen for the treatment of Vitamin B12 deficiency.

The present invention provides once weekly intranasal composition of methylcobalamin wherein a single dose administration of the composition to one nostril or each nostril provides required mean plasma concentration of cobalamin, without needing intervention of other dosage regimen in initial time points of therapy and thus provides a much needed patient friendly regimen for the treatment of vitamin B deficiency.

Preferably, the present invention provides once weekly intranasal composition of methylcobalamin comprising of about 2500 microgram/ml of methylcobalamin wherein intranasal administration of 100 microliters of the composition to each nostril of human, provides and maintains mean plasma concentration of cobalamin of about 200 pg/mL or more for at least 7 days.

The invention will be further illustrated by the following examples, however, without restricting its scope to these and other embodiments that a person skilled in the art in can arrive at by adapting and applying the invention in its numerous forms.

EXAMPLES

The following examples describe the invention in greater particularity and are intended to be a way of illustrating but not limiting the invention. Further, different strengths of the compositions and formulations thereof may be achieved by proportionately using a dose weight scale-up or scale-down formula. The concentrations of the ingredients, example an active constituent and excipients may also be varied or modified by a skilled artisan.

Example 1

The formulation suitable for intranasal administration was prepared as per the following composition and the method described below:

| S No | Ingredients | Concentration (W/V) |
|---|---|---|
| 1 | Methylcobalamin | 0.25% |
| 2 | Gellan gum | 0.40% |
| 3 | Hydroxypropylmethyl cellulose (HPMC) | 0.20% |
| 4 | Glycerin | 2.0% |
| 5 | Benzyl alcohol | 0.50% |
| 6 | Lecithin (Lipoid S-100) | 0.50% |
| 7 | Water for injection (vehicle) | Q.S. to 100% |

Glycerin was added and mixed with water for injection followed by addition of gellan gum and HPMC and dissolved completely. The prepared solution was heated up to 50° C. to which Lipoid S-100 was added. The solution was homogenized and autoclaved. To this, methylcobalamin was added and dissolved. Further, benzyl alcohol was added and water for injection was added to make up the final volume up to 100% and filled in container.

Example 2

The formulation suitable for intranasal administration was prepared as per the following composition and the method described below:

| S No | Ingredients | Concentration (W/V) |
|---|---|---|
| 1 | Methylcobalamin | 0.25% |
| 2 | Gellan gum | 0.40% |
| 3 | Hydroxypropylmethyl cellulose | 0.20% |
| 4 | Glycerin | 2.0% |
| 5 | Benzyl alcohol | 0.50% |
| 6 | Phenyl ethyl alcohol | 0.50% |
| 7 | Lecithin (Lipoid S-100) | 0.50% |
| 8 | Novamint Spearmint | 0.01-0.02% |
| 9 | Water for injection (Vehicle) | Q.S. to 100% |

Glycerin was added and mixed with water for injection followed by addition of gellan gum and HPMC and dissolved completely. The prepared solution was heated up to 50° C. to which Lipoid S-100 was added. The solution was homogenized and autoclaved. To this, benzyl alcohol, phenyl ethyl alcohol and methylcobalamin were added and dissolved. Further, Novamint Spearmint flavour was added and mixed. To the prepared solution, water for injection was added to make up the final volume up to 100% and filled in container.

Example 3

The formulation suitable for intranasal administration was prepared as per the following composition and the method described below:

| S No | Ingredients | Concentration (W/V) |
|---|---|---|
| 1 | Methylcobalamin | 0.25% |
| 2 | Gellan gum | 0.40% |
| 3 | Hydroxypropylmethyl cellulose (HPMC) | 0.20% |
| 4 | Glycerin | 2.0% |
| 5 | Benzyl alcohol | 0.50% |
| 6 | Phenyl ethyl alcohol | 0.50% |
| 7 | Lecithin (Lipoid S-100) | 0.50% |
| 8 | Water for injection (Vehicle) | Q.S. to 100% |

Glycerin was mixed with $CO_2$ purged cold water for injection and the solution was heated at 55° C. while continuing $CO_2$ purging till the step of autoclaving. Gellan gum and HPMC were added and mixed to the obtained solution. To this, Lipoid S-100 was added and homogenized for 30 minutes. The material was autoclaved for 15 minutes at 121° C. and cooled. Methylcobalamin, benzyl alcohol and phenyl ethyl alcohol were added and mixed with the obtained material. Further, water for injection was added to make up the volume up to 100%, cooled to 2-8° C., $CO_2$ purging was done and filled in container.

Example 4

Pharmacokinetic Study

A pharmacokinetic study of the formulation prepared as mentioned above under Example 1 was conducted in 8 human subjects.

200 microliters of (100 microliters each nostril) the composition according to Example 1 (having 2500 microgram/ml of methylcobalamin) was administered (Single administration) to 8 adult human beings.

Blood samples of subjects were collected at regular intervals: Pre-application and Post-application.

Sampling Hours: −14.00, 0.00 (Pre-application samples), 0.083, 0.16, 0.25, 0.50, 1.00, 2.00, 4.00, 8.00, 12.00, 26.00, 34.00, 50.00, 74.00, 98.00, 122.00, 146.00 and 170.00.

Mean plasma concentration of Cobalamin for the subjects at above mentioned time intervals can be seen in FIG. 1.

Cobalamin concentration was checked using Electrochemiluminescence method.

Observation

Nasal composition according to present invention increased total cobalamin concentration after first application above therapeutic level (200 pg/ml) and maintained up to 7 days.

We claim:

1. An intranasal composition comprising 10 mcg/ml to 4500 mcg/ml of methylcobalamin, gellan gum, and a permeation enhancer selected from lecithin and di-ethylene glycol monoethyl ether, wherein the composition forms an in-situ gel after intranasal administration.

2. The intranasal composition according to claim 1, wherein the composition comprises about 0.1-1% w/v of gellan gum.

3. The intranasal composition according to claim 1, wherein the composition comprises about 0.1-1% w/v of permeation enhancer.

4. The intranasal composition according to claim 1, wherein the composition further comprises excipients selected from thickening agent, humectant, preservative, flavoring agent and vehicle.

5. The intranasal composition according to claim 4, wherein the amount of thickening agent present is about 0.1% to about 1% w/v of the composition.

6. The intranasal composition according to claim 4, wherein the amount of humectant present is about 1% to about 5% w/v of the composition.

7. The intranasal composition according to claim 4, wherein the amount of preservative present is about 0.01 to about 1% w/v of the composition.

8. The intranasal composition according to claim 1, wherein the composition has a pH which ranges from 4 to 5.5.

9. The intranasal composition according to claim 1, wherein the composition is administered once weekly.

10. The intranasal composition according to claim 1, wherein the composition comprises about 2500 microgram/ml of methylcobalamin.

11. The intranasal composition according to claim 10, wherein an intranasal administration of 100 microliters of the composition to each nostril of human, provides and maintains mean plasma concentration of cobalamin of about 200 pg/mL or more for at least 7 days.

12. A method of treating vitamin B12 deficiency by intranasally administering a composition comprising 10 mcg/ml to 4500 mcg/ml of methylcobalamin, gellan gum and a permeation enhancer selected from lecithin and di-ethylene glycol monoethyl ether, wherein the composition forms in-situ gel after intranasal administration.

* * * * *